United States Patent [19]
Bhat et al.

[11] Patent Number: 6,100,428
[45] Date of Patent: Aug. 8, 2000

[54] NICKEL PROMOTED GUANYLATION OF AMINES WITH ISOTHIOUREAS AND THIOUREAS

[75] Inventors: Laxminarayan Bhat; Gunda I. Georg, both of Lawrence, Kans.

[73] Assignee: The University of Kansas, Lawrence, Kans.

[21] Appl. No.: 09/412,844

[22] Filed: Oct. 6, 1999

[51] Int. Cl.[7] ...................... C07C 279/16; C07C 279/18; C07C 279/24; C07C 271/20; C07C 303/40

[52] U.S. Cl. .................. 564/231; 544/159; 544/165; 544/167; 548/572; 548/575; 548/578; 560/25; 560/115; 560/158; 564/89; 564/90; 564/238

[58] Field of Search ...................... 544/159, 165, 544/167; 548/572, 575, 578; 560/25, 115, 158; 564/89, 90, 231, 238

[56] References Cited

U.S. PATENT DOCUMENTS 3,960,949  6/1976  Ahrens et al. ...................... 260/564 B

OTHER PUBLICATIONS

Lai, B., et al.; *Tetrahedron Lett.*, 37, pp. 2483–2486, 1996.
Su, W. *Synth. Commun.*, 26, pp. 407–413, 1996.
Kent, D.R., et al.; *Tetrahedron Lett.*, 37, pp. 8711–8714, 1996.
Monache, G.D., et al.; *J. Med. Chem.*, 36, pp. 2956–2963, 1993.
Smith, G.B.L.; *J. Am. Chem. Soc.*, 51, pp. 476–479, 1929.
Phillips, R., et al.; *J. Am. Chem. Soc.*, 45, pp. 1755–1757, 1923.
Lecher, H., et al.; *Chem. Ber.*, 56, pp. 1326–1330, 1923.
Levallet, C., et al.; *Tetrahedron*, 53, pp. 5291–5304, 1997.
Kim, K.S., et al.; *Tetrahedron Lett.*, 34, pp. 7677–7680, 1993.
Ramadas, K., et al.; *Tetrahedron Lett.,* 36, pp. 2841–2844, 1995.
Youg, Y.F., et al.; *J. Org. Chem.*, 62, pp. 1540–1542, 1997.
Poss, M.A., et al.; *Tetrahedron Lett.*, 33, pp. 5933–5936, 1992.
Manley, P.W., et al.; *J. Med. Chem.*, 35, pp. 2327–2340, 1992.
Olken, N.M., et al.; *J. Med. Chem.*, 35, pp. 1137–1144, 1992.
Farrario, F., et al.; *Synthetic Commun.*, 21, pp. 99–105, 1991.
Rasmussen, C.R., et al.; *Synthesis*, pp. 456–459, 1988.
Muller, G.W., et al.; *J. Med. Chem.,* 35, pp. 740–743, 1992.
Kim, K., et al.; *Tetrahedron Lett.*, 29, pp. 3183–3186, 1988.
Miller, A.E., et al.; *Synthesis*, pp. 777–779, 1986.
Maryanoff, C.A., et al.; *J. Org. Chem.*, 51, pp. 1882–1884, 1986.
Bernatowicz, M.S., et al.; *Synth. Commun.* 23, pp. 657–661, 1993.
Bernatowicz, M.S., et al.; *Tetrahedron Lett.*, 34, pp. 3389–3392, 1993.
Bernatowicz, M.S., et al.; *J. Org. Chem.*, 57, pp. 2497–2502, 1992.
Katrizky, A.R., et al.; *Synth. Commun.*, 25, pp. 1173–1186, 1995.
Feichtinger, K., et al.; *J. Org. Chem.*, 63, pp. 3804–3805, 1998.
Khurana, J.M., et al.; *Organic Preparations and Procedures Intl*, 29, pp. 1–32, 1997.
Ni, Z–J, et al.; *J. Org. Chem*, 56, pp. 4035–4042, 1991.
New Developments in Organonickel Chemistry. Symposia–in–Print graphical abstracts, *Tetrahedron*, 54, pp. 1021–1299, 1988.

*Primary Examiner*—Peter O'Sullivan
*Attorney, Agent, or Firm*—Hovey, Williams, Timmons & Collins

[57] ABSTRACT

An improved method for guanylating amines is provided. Broadly, the amines are reacted with a guanylating agent in the presence of a nickel catalyst. Preferably, the nickel catalyst comprises nickel in the zero oxidation state. Suitable nickel(0) catalysts are derived from nickel-boride alloys, nickel-phosphide alloys, aluminum-nickel alloys, nickel on kieselguhr, and nickel on silica/alumina catalysts. Preferred guanylating agents are thioureas and isothioureas. In one embodiment, protecting groups are selectively attached to the guanylating agents to yield particular substituted guanidines. The preferred protecting groups are Boc groups, Cbz groups, and arylsulfonyl groups. The reactions are particularly well suited for guanylating primary and secondary amines. The methods of the invention can be carried out under ambient conditions to provide high yields of the corresponding guanidines, with the nickel catalyst being essentially completely recoverable for reuse.

26 Claims, No Drawings

NICKEL PROMOTED GUANYLATION OF AMINES WITH ISOTHIOUREAS AND THIOUREAS

BACKGROUND OF THE INVENTION

1. Field of the Invention

The present invention is broadly concerned with methods of forming substituted guanidines utilizing nickel catalysts. More particularly, the methods comprise guanylating amines or pyrrolidines with guanylating agents such as thioureas or isothioureas in the presence of a nickel catalyst. Preferably, the nickel catalyst comprises nickel in the zero oxidation state. Suitable Ni(0) catalysts are preferably derived from nickel-boride alloys, nickel-phosphide alloys, aluminum-nickel alloys, nickel on kieselguhr, nickel on silica/alumina, and other nickel catalysts.

2. Description of the Prior Art

The guanidine functional group is an important structural component in many biologically active compounds. Due to their strongly basic character, guanidines are fully protonated under physiological conditions. The positive charge thus imposed on the molecule forms the basis for specific interactions between ligand and receptor or between enzyme and substrate, mediated by hydrogen bonds and/or electrostatic interactions. As a result, the guanidino group has been incorporated into many clinically useful drugs. For example, the guanidino group is used in $H_2$-receptor antagonists such as cimetidine and tiotidine which are anti-ulcer agents. The guanidine functional group is also found in cardiovascular drugs (e.g., clonidine, guanethidine), anti-diabetic drugs (e.g., phenformin, metformin), anti-malarial drugs (e.g., chloroguanidine), antibacterial agents (e.g., streptomycin), as well as other drugs.

Due to their importance in drug development, synthetic procedures for the preparation of guanidines under mild reaction conditions and in high yields while using minimal amounts of reagents are of significant interest to the pharmaceutical industry. Mild reaction conditions are necessary during the synthesis process because harsh conditions will lower the yield of the reaction product due to decomposition or unwanted side reactions of the valuable drug precursor. Reducing the number and quantity of reagents minimizes the quantity of reagent by-products generated which must be removed from the drug product, thus resulting in decreased drug production costs. Finally, of particular importance are chemical synthesis methods that minimize or eliminate the use of toxic reagents or catalysts, particularly in large scale industrial drug production.

Typically, synthesis of guanidines involves treating amines with guanylating agents. The most commonly used agents include derivatives of pyrazole-1-carboxamidine, aminoiminomethanesulfonic acid, S-methylisothiouronium salts, S-alkylisothioureas, and protected thiourea derivatives.

Substituted and protected thioureas are widely employed in the preparation of substituted guanidines. Coupling reagents (e.g., $Ph_3P/CCl_4$ and thiophilic metal salts such as HgO/S, $HgCl_2$, $CuCl_2$, and $CuSO_4$) have been extensively used in conjunction with thioureas for the guanylation of both aliphatic and aromatic amines. The initial step in these reactions involves the formation of intermediate carbodiimides which will then react with amines to give the corresponding guanidines. However, these reactions generally require an excess amount of reagents and/or longer reactions times in order to provide acceptable yields of the particular substituted guanidine. Furthermore, a distinct disadvantage to the use of mercuric salts in guanylation reactions is that the mercuric salts are toxic compounds. Finally, it is very difficult to separate the guanidines from the unreacted mercuric salts and the mercuric sulfide byproduct.

N-Unsubstituted S-methylisothioureas are useful for guanylating aliphatic primary and secondary amines. However, N-alkyl substituted S-methylisothioureas are inadequate at guanylating aliphatic primary and secondary amines due to the fact that this reaction is reversible and the byproduct methyl mercaptan must continually be removed from the reaction mixture in order to drive the reaction to completion.

There is a need for methods of guanylating amines in high yields which do not require the large quantities of coupling reagents and bases used in prior art methods.

SUMMARY OF THE INVENTION

The instant invention broadly comprises methods of forming substituted guanidines in the presence of a nickel catalyst. In more detail, guanylating agents are reacted with a compound selected from the group consisting of amines utilizing the nickel catalyst.

The nickel catalysts utilized in the inventive methods preferably comprise nickel in the zero oxidation state. Suitable Ni(0) catalysts are preferably derived from nickel-boride alloys, nickel-phosphide alloys, aluminum-nickel alloys, nickel on kieselguhr, and nickel on silica/alumina. Nickel catalysts are particularly advantageous due to their relatively inexpensive cost. Furthermore, the nickel catalysts are essentially completely recoverable after the guanylation reactions so that they may be reused. During the guanylation reactions, the nickel catalyst should be present at a level of less than about 10 molar % nickel, and preferably less than about 5 molar % nickel, based upon the total moles of guanylating agent(s) (e.g., isothioureas and/or thioureas) taken as 100%.

Preferred guanylating agents are thioureas and isothioureas, which have the respective general formulas

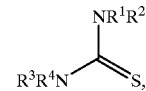

Formula I

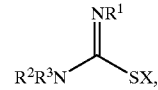

Formula II wherein each of $R^1$–$R^4$ is individually selected from the group consisting of hydrogen, protecting groups (i.e., a group which prevents the atom to which it is attached from reacting with any of the compounds present in the reaction mixture), aliphatic groups (branched and unbranched, preferably $C_1$–$C_{22}$), and cyclic groups (preferably aromatic), and wherein X is selected from the group consisting of aliphatic groups (preferably lower alkyl $C_1$–$C_4$ groups such as methyl groups) and cyclic groups (preferably aromatic or preferably $C_3$–$C_8$ aliphatic cyclic groups).

At least one of $R^1$–$R^4$ should preferably be a protecting group, and more preferably $R^1$ and $R^3$ are both protecting groups, with preferred protecting groups being selected from the group consisting of Boc groups (i.e., tert-butoxycarbonyl groups), Cbz groups (i.e., carbobenzyloxy groups), and arylsulfonyl groups. Arylsulfonyl groups include p-toluenesulfonyl groups and 4-methoxy-2,3,6-trimethylbenzylsulfonyl groups. Those skilled in the art will appreciate that the location of the particular protecting group(s) can be selected depending upon the desired final substituted guanidine. Particularly preferred protected thioureas and isothioureas include bis-Boc-protected thioureas and isothioureas. Of course, the protecting groups can be readily removed from the resulting guanidine using conventional methods.

In one embodiment, the methods of the invention comprise reacting a compound having the structure Formula I with an amine or pyrrolidine, wherein $R^1$ and $R^3$ of Formula I are Boc groups. In another embodiment, the invention comprises reacting a compound having the structure Formula II with an amine or pyrrolidine, wherein X of Formula II is selected from the group consisting of alkyl groups (and particularly methyl groups) and benzyl groups. Even more preferably, in this latter embodiment $R^1$ and $R^2$ of Formula II are phenyl.

In another embodiment, the methods of the invention comprise reacting pyrrolidine with a compound selected from the group consisting of

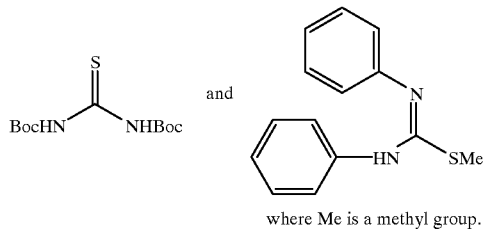

where Me is a methyl group.

Particularly preferred thioureas and isothioureas are those selected from the group consisting of

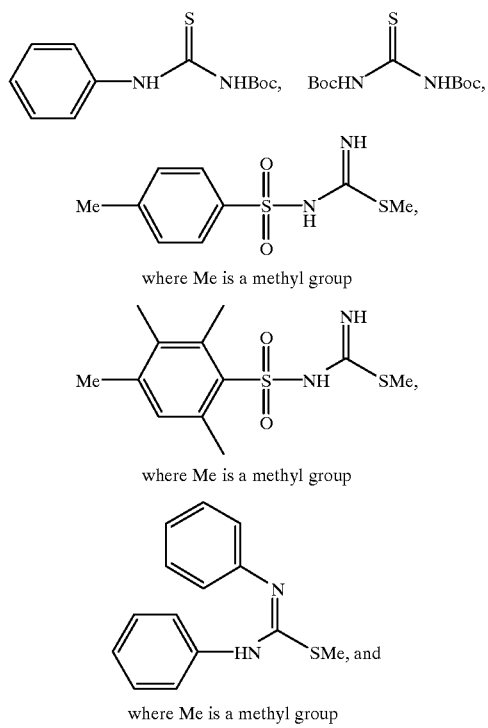

where Me is a methyl group where Me is a methyl group where Me is a methyl group -continued

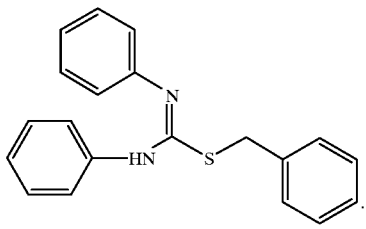

While essentially any amine can be reacted with a guanylating agent in the presence of a nickel catalyst according to the invention, preferred amines are primary and secondary amines. Specific amines which work well with the instant methods include those selected from the group consisting of

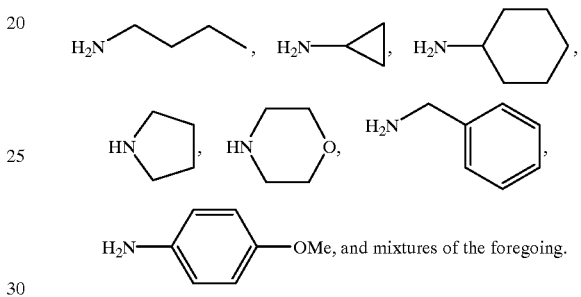

-OMe, and mixtures of the foregoing.

The inventive reactions are preferably carried out at a temperature of from about −30–140° C., and more preferably at room temperature or under ambient conditions. It is preferable that the reaction be carried out in a solvent system. Suitable solvent systems comprise a solvent selected from the group consisting of DMF, THF, DMSO, and water mixed with any of the foregoing. Carrying out the reactions with a nickel catalyst and a thiourea as the guanylating agent will result in a percent yield (based upon the theoretical yield) of at least about 10%, preferably at least about 40%, and more preferably at least about 85%, after a reaction time of about 30 minutes. Carrying out the reactions with a nickel catalyst and an isothiourea as the guanylating agent will result in a percent yield (based upon the theoretical yield) of at least about 10%, preferably at least about 40%, and more preferably at least about 85%, after a reaction time of about 2 hours.

DETAILED DESCRIPTION OF THE PREFERRED EMBODIMENTS

The methods of the instant invention can be utilized to synthesize N-substituted and N,N-disubstituted guanidines from bis-protected thioureas in the presence of a nickel catalyst. Suitable protecting groups include Boc groups and Cbz groups. The N protecting groups can be easily cleaved from the resulting guanidines under mild reaction conditions. These bis-protected thioureas can be utilized to guanylate both aromatic and aliphatic primary and secondary amines at room temperature with high yields. A general reaction scheme by which this guanylation takes place is shown in Scheme 1.

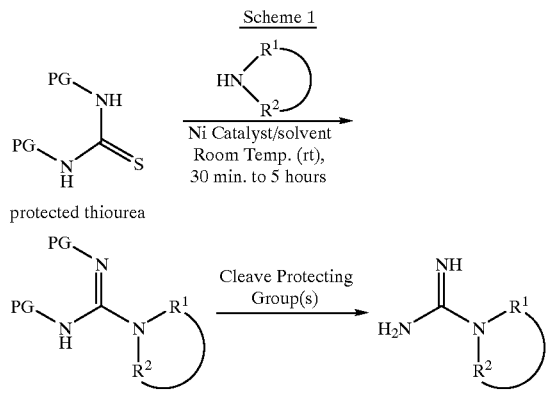

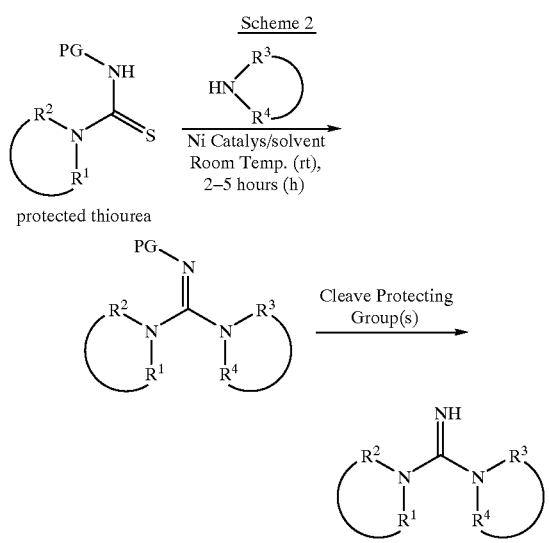

Those skilled in the art will appreciate that mono-, di-, tri-, and tetrasubstituted guanidines can be synthesized from N-protected thioureas in the presence of a nickel catalyst such as nickel-boride (nickel boride, nickel-boride, nickel boride alloy, and nickel-boride alloy are used interchangeably herein to refer to alloys comprising nickel and boride). Suitable protecting groups again include Boc and Cbz, as well as an N-arylsulfonyl group. These protected thioureas can be used to guanylate both aromatic and aliphatic amines. One general reaction by which this guanylation occurs is shown in Scheme 2.

N-Arylsulfonyl protected methylisothioureas can also be used to guanylate aliphatic and aromatic amines in the presence of a nickel catalyst. A general outline of this reaction is shown in Scheme 3.

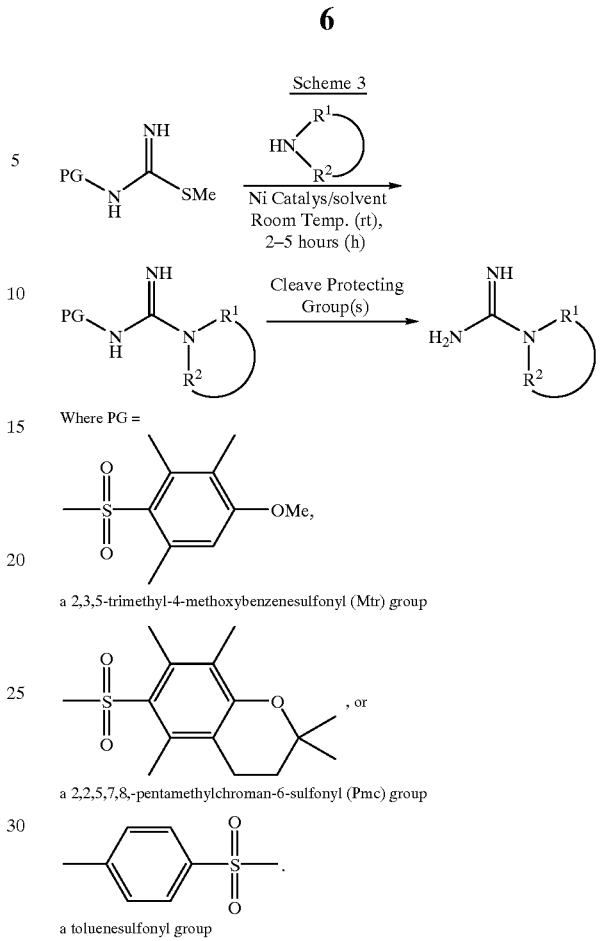

1,3-diphenyl-S-methylisothiourea can be used to guanylate aliphatic and cyclic amines in the presence of a nickel catalyst. A general outline of this reaction is shown in Scheme 4.

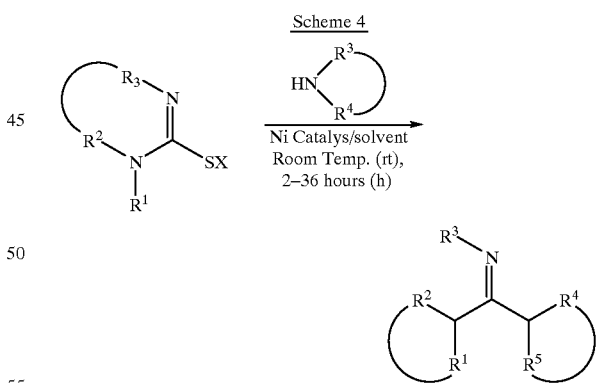

While it is possible that the inventive guanylation reactions take place via a carbodiimide intermediate, because the reactions are taking place under neutral conditions it is believed that the mechanism by which the nickel catalyst promotes guanylation reactions is similar to that described by Ni et al., Nickel-Catalyzed Olefination of Cyclic Benzylic Dithioacetals by Grignard Reagents, *J. Org. Chem.* 56:4035–42 (1991), incorporated by reference herein. That is, it is believed that the nickel(0) species initially coordinates with the divalent sulfur of thiourea and then undergoes oxidative insertion of nickel into the carbon-sulfur double bond to give the three-membered cyclic intermediate Formula III shown in Scheme 5.

Scheme 5

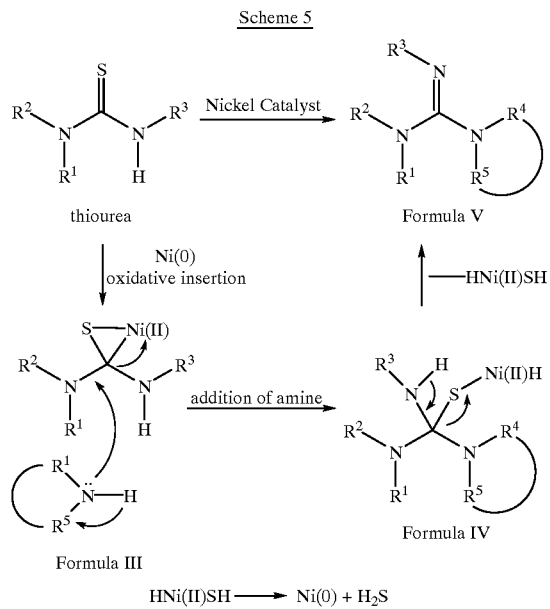

The highly reactive cyclic intermediate Formula III yields the complex designated by Formula IV as a result of the nucleophilic attack of the amine and breaking of the carbon-nickel bond. Cleavage of the carbon-sulfur bond by elimination of the proton on the adjacent nitrogen forms the Formula V guanidine and a hydrido nickel(II) complex (which thermally decomposes to regenerate the Ni(0) species). A similar mechanism is believed to occur when the guanylating agent is a isothiourea.

EXAMPLES

The following examples set forth preferred methods in accordance with the invention. It is to be understood, however, that these examples are provided by way of illustration and nothing therein should be taken as a limitation upon the overall scope of the invention.

Example 1

Synthesis of Isothioureas and Thioureas

1. N,N'-Bis-tert-butoxycarbonylthiourea

Isothioureas were prepared for use in the exemplary guanylation reactions. N,N'-bis-tert-butoxycarbonylthiourea was prepared according to the protocol reported by Iwanowicz et al., Preparation of N,N'-Bis-tert-Butoxycarbonylthiourea, *Synth. Commun.*, 23:1443–45 (1993). The reaction by which the N,N'-bis-tert-butoxycarbonylthiourea was formed is outlined in Scheme A.

Scheme A

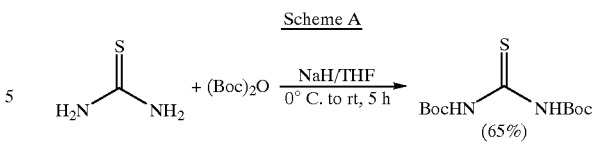

Wherein Boc refers to tert-butoxycarbonyl.

2. N-Arylsulfonyl-S-methylisothiourea

N-Arylsulfonyl-S-methylisothiourea was prepared as described by Kent et al., Two New Reagents for the Guanylation of Primary, Secondary and Aryl Amines, *Tetrahedron Lett.*, 37:8711–14 (1996). This reaction is outlined in Scheme B.

Scheme B

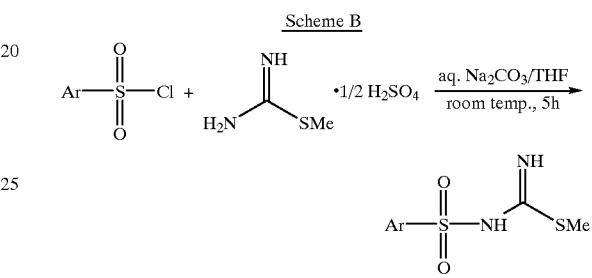

Ar =

p-tolyl group: yield = 65%

4-methoxy-2,3,6-trimethylphenyl group: yield = 68%

3. Synthesis of N,N'-diphenyl-S-benzylisothioureas and N,N'-diphenyl-S-methylisothioureas A solution of halide (55 mmol) in acetone (25 ml) was added dropwise to a stirred suspension of thiocarbanilide (11.40 g, 50 mmol) and potassium carbonate (6.90 g, 50 mmol). The reaction mixture was stirred at ice bath temperature for about 30 minutes, followed by stirring at room temperature. The progress of the reaction was monitored by TLC. The reaction mixture was then filtered and the resulting precipitate washed 3 times with 15 ml portions of acetone. The combined filtrates were concentrated on a rotavapor. The residue was diluted with methylene chloride (100 ml) followed by two washings with 25 ml portions of water. The residue was then dried over sodium sulfate. The crude product was purified by passing it through a short silica gel column using a gradient of hexane and diethyl ether as eluents. Scheme C and its accompanying table outline the general reaction which took place as well as the halides used, the isothioureas resulting from the reaction, and the yield of those isothioureas.

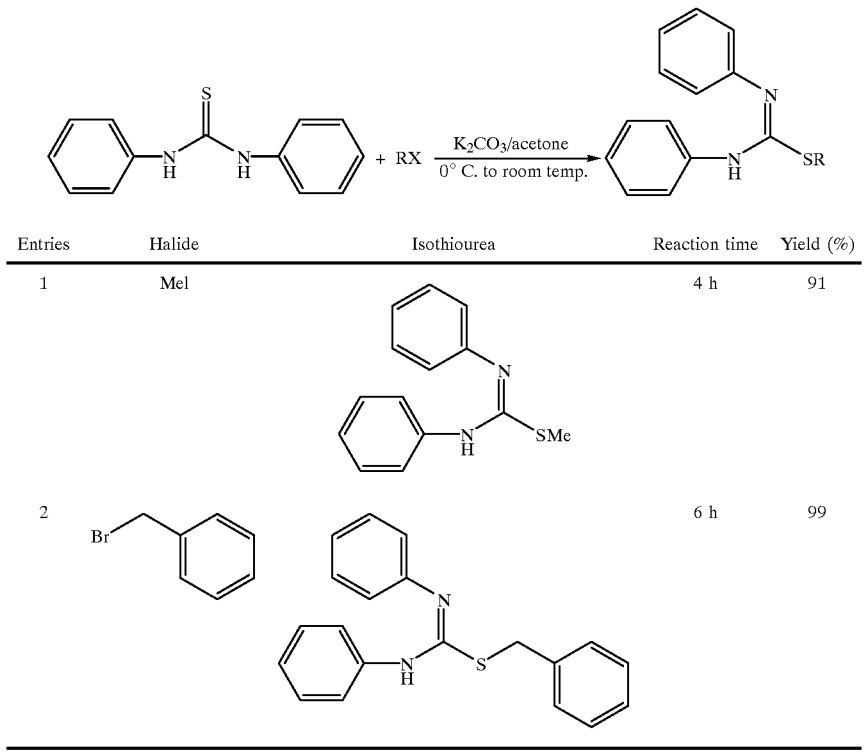

Example 2

Synthesis of N,N'-bis-tert-butoxycarbonyl Protected Guanidines Guanylation of Amines Nickel-boride alloy (13 mg, 0.10 mmol, prepared by the reduction of nickel acetate or chloride with sodium borohydride in ethanol or water) was added to a solution of N,N'-bis-tert-butoxycarbonylthiourea (28 mg, 0.10 mmol, prepared in Part 1 of Example 1) and an amine (0.15 mmol) in dimethyl formamide (DMF) contained in a 15 ml screw cap vial. The solution was stirred at room temperature and the progress of the reaction was monitored by thin layer chromatography (TLC). The reaction mixture was then diluted with ethyl acetate (15 ml) and poured into 25 ml of water. The organic layer was separated, and the aqueous layer was extracted with 10 ml of ethyl acetate. The combined extracts were washed twice with 15 ml of water after which they were dried over sodium sulfate, evaporating the solvent. The residue was passed through a short silica gel column using a gradient of hexane and ether as eluents to give the pure guanidine. The general reaction is outlined in Scheme D. The particular amines utilized in the respective preparations as well as the reactions times, resulting guanidines, and yields of those guanidines are set forth in Table 1.

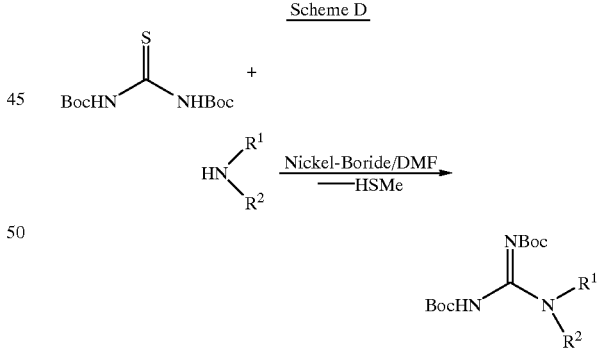

TABLE 1

Guanylation of amines with N,N'-bis-tert-butoxycarbonylthiourea.

| Entries | Amine | Guanidine | Reaction time | Reaction temp | Yield (%) |
|---|---|---|---|---|---|
| 1 | H₂N-butyl | BocHN-C(=NBoc)-NH-butyl | 90 min | room temp. | 91 |
| 2 | H₂N-cyclopropyl | BocHN-C(=NBoc)-NH-cyclopropyl | 90 min | room temp. | 94 |
| 3 | H₂N-cyclohexyl | BocHN-C(=NBoc)-NH-cyclohexyl | 2 h | room temp. | 97 |
| 4 | pyrrolidine (HN) | BocHN-C(=NBoc)-N(pyrrolidine) | 2 h | room temp. | 89 |
| 5 | morpholine (HN-O) | BocHN-C(=NBoc)-N(morpholine) | 3 h | room temp. | 91 |
| 6 | H₂N-CH₂-Ph | BocHN-C(=NBoc)-NH-CH₂-Ph | 90 min | room temp. | 92 |

Guanylation reactions of pyrrolidine with N,N'-bis-tert-butoxycarbonylthiourea were carried out under various reaction conditions utilizing a variety of solvents in order to optimize the suitable solvent conditions to run this reaction ("THF" refers to tetrahydrofuron and "DMSO" refers to dimethyl sulfoxide). The aqueous layer extraction was effected with methylene chloride rather than with ethyl acetate as was the case in Part 1 above. Scheme E outlines the general reaction while Table 2 sets forth the various solvents tested, reaction conditions, and the % yield of guanylated pyrrolidine. DMSO and DMSO-H₂O (Entries 4 and 5, respectively) were the most effective solvents.

Scheme E

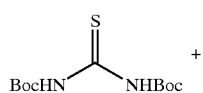

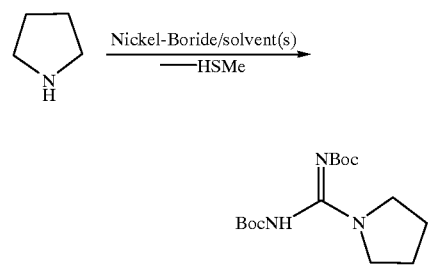

TABLE 2

Guanylation of pyrrolidine with N,N'-bis-tert-butoxycarbonylthiourea in different reaction conditions.

| Entries | Solvent(s) | Reaction time | Reaction temp. | Yield (%) |
|---|---|---|---|---|
| 1 | DMF | 2 h | room temp. | 89 |
| 2 | THF | 3 h | room temp. | 100 |
| 3 | THF-H₂O (3:1) | 1 h | room temp. | 100 |
| 4 | DMSO | 1 h | room temp. | 100 |

TABLE 2-continued

Guanylation of pyrrolidine with N,N'-bis-tert-butoxycarbonylthiourea in different reaction conditions.

| Entries | Solvent(s) | Reaction time | Reaction temp. | Yield (%) |
|---|---|---|---|---|
| 5 | DMSO-H₂O (3:1) | 45 min | room temp. | 100 |

Example 3

Synthesis of N-tosyl and N-mtr Protected Guanidines

Nickel-boride alloy (13 mg, 0.10 mmol) was added to a stirred solution of N-arylsulfonyl-S-methylisothiourea (0.10 mmols, prepared in Part 2 of Example 1) and an amine (0.15 mmol) in DMF contained in a 15 ml screw cap vial. The reaction mixture was heated in a sand bath, and the progress of the reaction was monitored by TLC. After completion of the reaction, the mixture was cooled to room temperature followed by dilution with 15 ml of ethyl acetate. The reaction mixture was poured into 25 ml of water, and the organic layer was separated. The aqueous layer was extracted with 10 ml of ethyl acetate, and the combined extracts were washed twice with 15 ml of water. The solvent was then evaporated by drying over sodium sulfate. The crude product was purified by passing the product through a short silica gel column using hexane and diethyl ether as eluents. Tables 3 and 4 set forth the particular amines which were guanylated in this series of tests as well as the resulting guanidines and percent yields of those guanidines. Schemes F and G outline the general reaction taking place when guanidine is reacted with the particular N-arylsulfonyl-S-methylisothiourea.

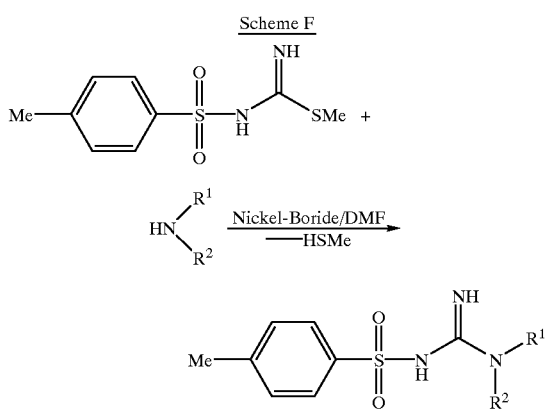

Scheme F

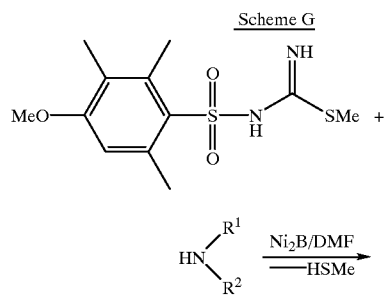

Scheme G

TABLE 3

Guanylation of amines with N-(p-toluenesulfonyl)-S-methylisothiourea.

| Entries | Amine | Guanidine | Reaction time | Reaction temp. | Yield (%) |
|---|---|---|---|---|---|
| 1 | H₂N-CH₂-C₆H₅ | Me-C₆H₄-SO₂-NH-C(=NH)-NH-CH₂-C₆H₅ | 8 h | 100° C. | 79 |
| 2 | morpholine (HN) | Me-C₆H₄-SO₂-NH-C(=NH)-N(morpholine) | 10 h | 100° C. | 91 |
| 3 | H₂N-C₆H₄-OMe | Me-C₆H₄-SO₂-NH-C(=NH)-NH-C₆H₄-OMe | 18 h | 100° C. | 85 |

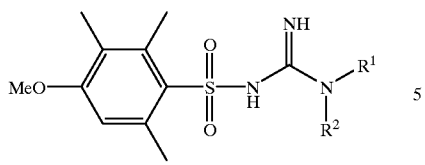

TABLE 4

Guanylation of amines with N-(2,3,6-trimethyl-4-methoxybenzene sulfonyl)-S-methylisothiourea.

| Entries | Amine | Guanidine | Reaction time | Reaction temp. | Yield (%) |
| --- | --- | --- | --- | --- | --- |
| 1 | H₂N–CH₂–C₆H₅ | MeO-aryl-SO₂-NH-C(=NH)-NH-CH₂-C₆H₅ | 26 | 90° C. | 89 |
| 2 | pyrrolidine | MeO-aryl-SO₂-NH-C(=NH)-N(pyrrolidinyl) | 18 | 90° C. | 92 |
| 3 | H₂N–C₆H₄–OMe | MeO-aryl-SO₂-NH-C(=NH)-NH-C₆H₄-OMe | 36 | 90° C. | 78 |

Example 4

Guanylation of Amines with N,N'-diphenyl-S-methylisothiourea and N,N'-diphenyl-S-benzylisothiourea Nickel-boride alloy (13 mg, 0.10 mmol) was added to a solution of N,N'-diphenyl-S-methylisothiourea (24 mg, 0.10 mmol, prepared in Part 3 of Example 1) and an amine (0.15 mmol) in DMF contained in a 15 ml screw cap vial. The mixture was heated in a sand bath, and the progress of the reaction was monitored by TLC. After completion of the reaction, the reaction mixture was cooled to room temperature and diluted with ethyl acetate (15 ml). The organic layer was separated, and the aqueous layer was extracted with 10 ml of ethyl acetate. The combined organic extracts were washed twice with 15 ml portions of water, followed by drying over sodium sulfate. The residue was passed through a short silica gel column using a gradient of hexane and ethyl acetate as eluents to give the corresponding pure guanidine.

Scheme H outlines the general reaction scheme when aliphatic and benzylic amines were guanylated with N,N'-diphenyl-S-methylisothiourea. Table 5 lists the particular amines that were guanylated as well as the resulting guanidines and the yields of those guanidines.

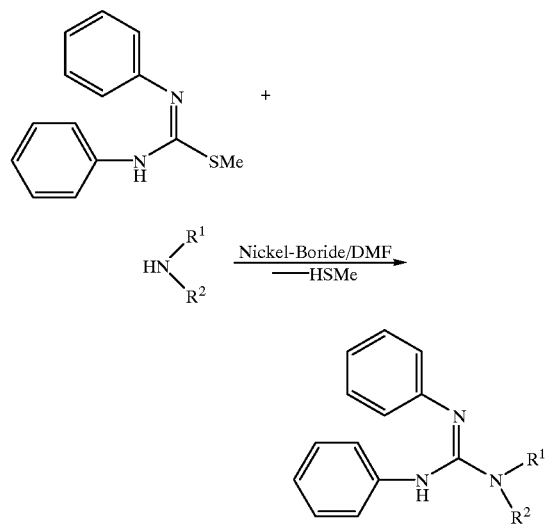

Scheme H

TABLE 5

Guanylation of aliphatic and benzylic amines with N,N'-diphenyl-S-methylisothiourea.

| Entries | Amine | Guanidine | Reaction time | Reaction temp. | Yield (%) |
|---|---|---|---|---|---|
| 1 | n-butylamine | N,N'-diphenyl-N''-butylguanidine | 8 h | 80° C. | 96 |
| 2 | isopropylamine | N,N'-diphenyl-N''-isopropylguanidine | 15 h | 80° C. | 98 |
| 3 | tert-butylamine | N,N'-diphenyl-N''-tert-butylguanidine | 18 h | 80° C. | 98 |
| 4 | diisopropylamine | N,N'-diphenyl-N'',N''-diisopropylguanidine | 18 h | 80° C. | 95 |
| 5 | pyrrolidine | N,N'-diphenyl-pyrrolidinylguanidine | 3 h | 100° C. | 95 |
| 6 | morpholine | N,N'-diphenyl-morpholinylguanidine | 17 h | 100° C. | 97 |

TABLE 5-continued

Guanylation of aliphatic and benzylic amines with N,N'-diphenyl-S-methylisothiourea.

| Entries | Amine | Guanidine | Reaction time | Reaction temp. | Yield (%) |
|---|---|---|---|---|---|
| 7 | 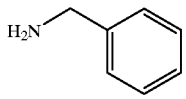 | 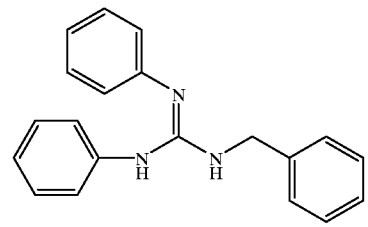 | 7 h | 100° C. | 94 |
| 8 | 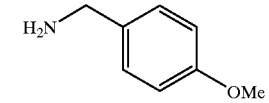 | 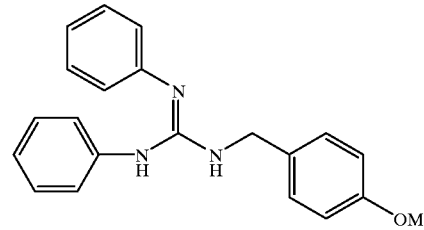 | 7 h | 100° C. | 95 |

The guanylation of aromatic amines with N,N'-diphenyl-S-methylisothiourea is outlined in Scheme I, while Table 6 sets forth the particular amines which were guanylated as well as the resulting guanidines. Methylene chloride was utilized during the work-up procedures in place of ethyl acetate in these procedures.

Scheme I

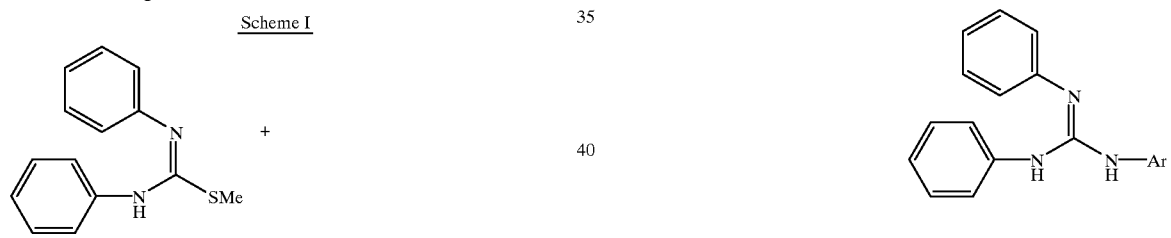

TABLE 6

Guanylation of aromatic amines with N,N''-diphenyl-S-methylisothiourea.

| Entries | Amine | Guanidine | Reaction time | Reaction temp. | Yield (%) |
|---|---|---|---|---|---|
| 1 | 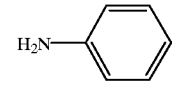 | 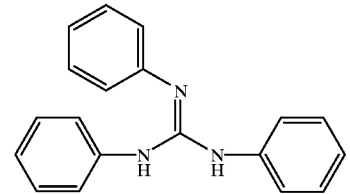 | 6 h | 65° C. | 98 |

TABLE 6-continued

Guanylation of aromatic amines with N,N''-diphenyl-S-methylisothiourea.

| Entries | Amine | Guanidine | Reaction time | Reaction temp. | Yield (%) |
|---|---|---|---|---|---|
| 2 | H₂N—⟨C₆H₄⟩—OMe | [Ph-N=C(NHPh)(NH-C₆H₄-OMe)] | 15 h | 65° C. | 89 |
| 3 | 2,6-Cl₂-C₆H₃-NH₂ | [Ph-N=C(NHPh)(NH-2,6-Cl₂C₆H₃)] | 15 h | 65° C. | 91 |

Scheme J outlines guanylation reactions of pyrrolidine with N,N'-diphenyl-S-methylisothiourea in various solvents. Table 7 sets forth the particular solvents that were utilized. Methylene chloride was used during the work-up procedures in place of ethyl acetate in this set of procedures.

Scheme K shows the general reaction for the guanylation of amines with N,N'-diphenyl-S-benzylisothiourea, while Table 8 sets forth the structure of the particular amines that were guanylated as well as the resulting guanidines and their respective percent yields.

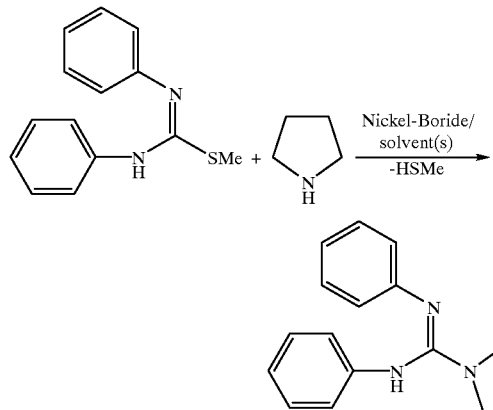

Scheme J

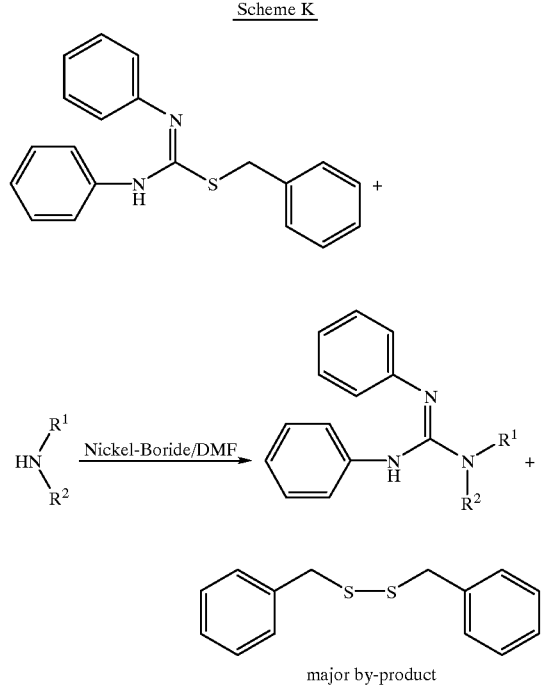

Scheme K

TABLE 7

Guanylation of pyrrolidine with N,N'-diphenyl-S-methylisothiourea in different reaction conditions.

| Entries | Solvent(s) | Reaction time | Reaction temp. | Yield (%) |
|---|---|---|---|---|
| 1 | DMF | 3 h | 100° C. | 95 |
| 2 | THF | 5 h | 60° C. | 100 |
| 3 | THF-H₂O (3:1) | 3 h | 60° C. | 100 |
| 4 | DMSO | 18 h | room temp. | 100 |
| 5 | DMSO-H₂O (3:1) | 4 h | room temp. | 100 |

TABLE 8

Guanylation of amines with N,N"-diphenyl-S-benzylisothiourea.

| Entries | Amine | Guanidine | Reaction time | Reaction temp. | Yield (%) |
|---|---|---|---|---|---|
| 1 | pyrrolidine (HN) | N,N'-diphenyl-pyrrolidine guanidine | 8 h | 80° C. | 91 |
| 2 | H₂N-CH₂-phenyl | N,N'-diphenyl-N"-benzyl guanidine | 10 h | 80° C. | 88 |

EXAMPLE 5

Guanylation of Pyrrolidine in Presence of Varying Molar Concentrations of Nickel-Boride N,N'-Bis-tert-butoxycarbonylthiourea was prepared as described in Part 1 of Example 1. Pyrrolidine was then guanylated at room temperature as described in Part 2 of Example 2 during the course of five test runs, with nickel-boride being present at nickel molar percents of 100 mol %, 50 mol %, 25 mol %, 10 mol %, and 5 mol % (all based on the total moles of N,N'-Bis-tert-butoxycarbonylthiourea taken as 100% by weight), respectively, during the test runs. The reaction scheme followed was identical to Scheme E above, with DMSO being the solvent. Table 9 sets forth the results of these runs.

TABLE 9

Guanylation of pyrrolidine with N,N'-bis-tert-butoxycarbonylthiourea in the presence of varying molar concentrations of nickel-boride.

| Entries | Nickel-Boride (mol %)[a] | Reaction Time | Yield (%) |
|---|---|---|---|
| 1 | 100 | 1 h | 100 |
| 2 | 50 | 1 h | 100 |
| 3 | 25 | 1½ h | 100 |
| 4 | 10 | 2 h | 100 |
| 5 | 5 | 4 h | 100 |

[a]Nickel molar percent based upon the total moles of N,N'-Bis-tert-butoxycarbonylthiourea as 100%.

These results indicate that the nickel(0) derived from the nickel-boride acts as a catalyst during the guanylation reactions.

EXAMPLE 6

Guanylation of Pyrrolidine in the Presence of Various Nickel Catalysts

In this example, several commercially available nickel catalysts were tested to determine their effectiveness. Those catalysts were: nickel-phosphide alloy; aluminum-nickel alloy; nickel on kieselguhr; and nickel on silica/alumina. In each of the tests, 1 equivalent of N,N'-bis-tert-butoxycarbonylthiourea, 1.5 equivalents of pyrrolidine, and 1 equivalent of nickel catalyst in DMSO were utilized. Each reaction was carried out at room temperature. The data from these tests are recorded in Table 10.

TABLE 10

Guanylation of Pyrrolidine with N,N'-bis-tert-butoxycarbonylthiourea in the presence of various nickel catalysts.

| Entries | Nickel Catalyst | Reaction Time | Yield (%) |
|---|---|---|---|
| 1 | nickel-phosphide | 1 h | 100 |
| 2 | aluminum-nickel | 1 h | 100 |
| 3 | nickel, ~60 wt. % on kieselguhr | 45 min. | 100 |
| 4 | nickel, ~65 wt. % on silica/alumina | 30 min. | 100 |

All of the nickel catalysts worked well and gave the corresponding guanidines in quantitative yields. The reactions were much faster when nickel on silica/alumina and nickel on kieselguhr were utilized as the catalysts compared to nickel-phosphide and aluminum nickel catalysts, with the reaction utilizing nickel on silica/alumina being extremely rapid. Commercially, aluminum-nickel catalysts will likely be the most important due to their relatively low cost. Finally, in comparing these results to those of Example 5, the catalysts listed in Table 10 would be effective in catalytic amounts as was the case with the nickel-boride.

We claim:

1. A method of forming a compound comprising a guanidine, the method comprising the steps of:

(a) providing a compound having a formula selected from the group consisting of

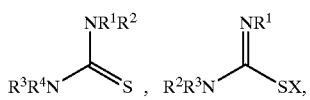

wherein each of $R^1$–$R^4$ is individually selected from the group consisting of hydrogen, protecting groups, aliphatic groups, and cyclic groups, and wherein X is selected from the group consisting of hydrogen, aliphatic groups and cyclic groups; and (b) causing the compound of step (a) to react, in the presence of a catalyst comprising nickel, with an amine so as to yield the guanidine compound.

2. The method of claim 1, wherein said catalyst comprises nickel in its zero oxidation state.

3. The method of claim 1, wherein at least one of $R^1$–$R^4$ is a protecting group.

4. The method of claim 3, wherein said protecting group is selected from the group consisting of Boc groups, Cbz groups, and arylsulfonyl groups.

5. The method of claim 4, wherein said protecting group is an arylsulfonyl group selected from the group consisting of p-toluenesulfonyl groups and 4-methoxy-2,3,6-trimethylbenzylsulfonyl groups.

6. The method of claim 1, wherein step (a) comprises providing a compound having a formula selected from the group consisting of

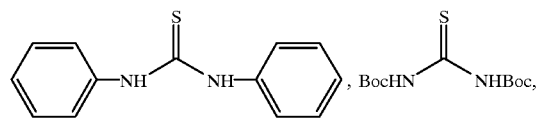

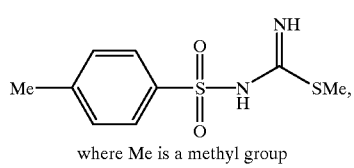

where Me is a methyl group

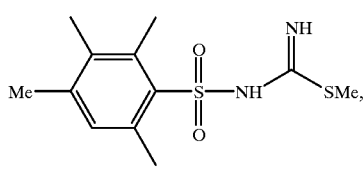

where Me is a methyl group

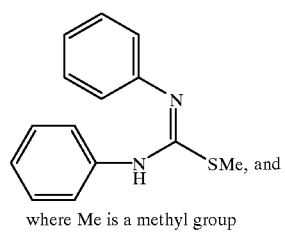

where Me is a methyl group

-continued

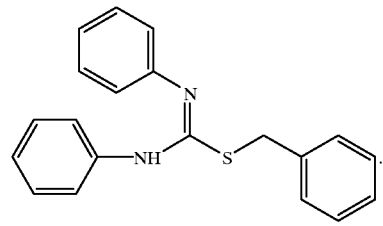

7. The method of claim 1, wherein said amine is selected from the group consisting of primary and secondary amines and mixtures thereof.

8. The method of claim 7, wherein said amine is selected from the group consisting of

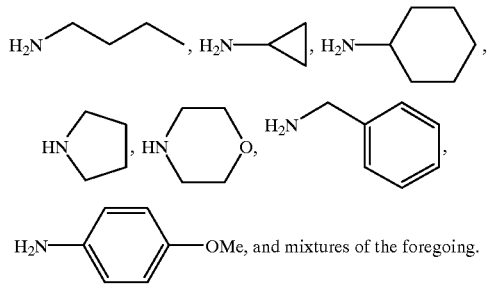

9. The method of claim 1, wherein said catalyst is selected from the group consisting of nickel-phosphide, nickel-boride, aluminum-nickel, nickel on kieselguhr, and nickel on silica/alumina catalysts.

10. The method of claim 1, wherein the compound provided in step (a) has the formula

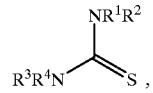

and the percent yield of the guanidine compound resulting from step (b) is at least about 40% after a reaction time of about 30 minutes.

11. The method of claim 1, wherein the compound provided in step (a) has the formula

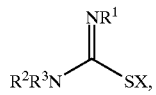

and the percent yield of the guanidine compound resulting from step (b) is at least about 40% after a reaction time of about 2 hours.

12. The method of claim 1, wherein step (b) is carried out at a temperature of from about −30–40° C.

13. The method of claim 1, wherein step (b) is carried out under ambient conditions.

14. The method of claim 1, wherein step (b) is carried out in a solvent system.

15. The method of claim 14, wherein said solvent system comprises a solvent selected from the group consisting of DMF, THF, DMSO, and water mixed with any of the foregoing.

16. The method of claim 1, wherein said nickel catalyst is present during step (b) at a nickel molar ratio of less than about 10%, based upon the total moles of the compound provided in step (a) taken as 100% by weight.

17. The method of claim 3, further including the step of removing the protecting group from the guanidine compound.

18. The method of claim 1, wherein said compound provided in step (a) has the formula

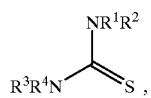

and wherein each of $R^1$ and $R^3$ is a hydrogen and each of $R^2$ and $R^4$ is a protecting group.

19. The method of claim 1, wherein said compound provided in step (a) has the formula

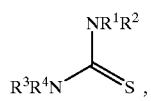

and wherein each of $R^1$ and $R^3$ is individually selected from the group consisting of alkyl groups, aryl groups, and hydrogen.

20. The method of claim 1, wherein said compound provided in step (a) has the formula

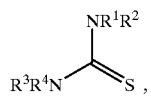

and wherein one of $R^1$–$R^4$ is a protecting group, and the others of $R^1$–$R^4$ are each individually selected from the group consisting of alkyl groups, aryl groups, and hydrogen.

21. The method of claim 1, wherein said compound provided in step (a) has the formula

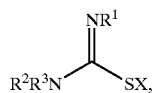

wherein X is selected from the group consisting of alkyl groups and benzyl groups.

22. The method of claim 21, wherein X is a methyl group.

23. The method of claim 21, wherein each of $R^1$ and $R^2$ is benzene.

24. The method of claim 21, wherein $R^2$ is selected from the group consisting of p-toluenesulfonyl groups and 4-methoxy-2,3,6-trimethylbenzylsulfonyl groups.

25. The method of claim 1, wherein said compound provided in step (a) is selected from the group consisting of

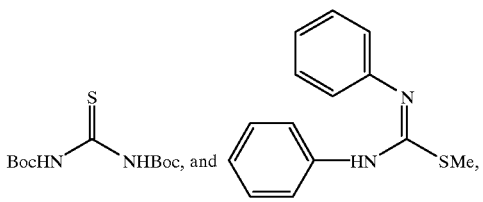

wherein Me is a methyl group, and wherein said amine comprises pyrrolidine.

26. The method of claim 1, wherein X is a methyl group.

* * * * *